US007314757B2

(12) United States Patent
Medrano et al.

(10) Patent No.: US 7,314,757 B2
(45) Date of Patent: Jan. 1, 2008

(54) DROUGHT INDUCIBLE PROMOTERS AND USES THEREOF

(75) Inventors: Leonard Medrano, Azusa, CA (US); Kenneth A. Feldmann, Newbury Park, CA (US); Nickolai Alexandrov, Thousand Oaks, CA (US); Yiwen Fang, Los Angeles, CA (US); Nester Apuya, Culver City, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/305,713

(22) Filed: Dec. 16, 2005

(65) Prior Publication Data

US 2006/0143739 A1 Jun. 29, 2006

Related U.S. Application Data

(60) Provisional application No. 60/637,269, filed on Dec. 16, 2004.

(51) Int. Cl.
*A01H 1/00* (2006.01)
*C07H 21/04* (2006.01)
*C12N 5/14* (2006.01)
*C12N 15/09* (2006.01)

(52) U.S. Cl. .................. 435/468; 435/320.1; 435/419; 435/6; 435/69.1; 536/24.1; 536/23.1; 800/278; 800/295

(58) Field of Classification Search ............... None
See application file for complete search history.

(56) References Cited

U.S. PATENT DOCUMENTS

| | | | |
|---|---|---|---|
| 6,429,307 B1 | 8/2002 | Yoshiba et al. | |
| 2002/0160378 A1* | 10/2002 | Harper et al. | ........... 435/6 |
| 2004/0123347 A1 | 6/2004 | Hinchey et al. | |

OTHER PUBLICATIONS

Kim et al. (Plant Molecular Biology, 24:105-117, 1994).*
Database EMBL [Online], *Arabidopsis thaliana* chromosome 2 clone . . . , Database Accession No. AC005662. XP002378270.
Nakashima, Kazuo et al., "Organization and expression of two *Arabidopsis* . . . ," Plant Molecular Biology, 2000, 42, pp. 657-665.
Yamaguchi-Shinozaki, Kazuko et al., "Regulation of genes that are Induced . . . ," J. Plant. Res. 1995, 108, pp. 127-136.
Guerrero, Felix D. et al., "Tissue-specific expression of a plant turgor-responsive . . . ," Plant Molecular Biology, 1993, 21, pp. 929-935.
Nakashima, Kazuo et al., "A nuclear gene, erd1, encoding a chloroplast-targeted . . . ," The Plant Journal, 1997, 12(4), pp. 851-861.
Xu et al., "A wheat (*Triticum aestivum*) protein phosphatase 2A catalytic subunit gene provides enhanced drought tolerance in tobacco", Ann Bot (Lond.), Mar. 2007;99(3):439-50.

Brini et al, "Overexpression of wheat Na+/H+ antiporter TNHX1 and H+- pyrophosphatase TVP1 improve salt- and drought-stress tolerance in *Arabidopsis thaliana* plants", J. Exp Bot. 2007;58(2):301-8.
Zhang et al, "Cloning and characterization of a putative 12-oxophytodienoic acid reductase cDNA induced by osmotic stress in roots of foxtail millet", DNA seq., Apr. 2007;18(2):138-44.
Zhang et al., "Heterologous expression of two Medicago truncatula putative ERF transcription factor genes, WXP1 and WXP2, in *Arabidopsis* led to increased leaf wax accumulation and improved drought tolerance, but differential response in freezing tolerance", Plant Mol Biol, Mar. 9, 2007.
Qin et al, "Regulation and functional analysis of ZmDREB2A in response to drought and heat stresses in *Zea mays* L.", Plant J., Apr. 2007;50(1):54-69.
Dai et al., "Overexpression of an R1R2R3 MYB Gene, OsMYB3R-2, Increases Tolerance to Freezing, Drought, and Salt Stress in Transgenic *Arabidopsis*", Plant Physiol., Apr. 2007;143(4):1739-51.
Tran et al., "Co-expression of the stress-inducible zinc finger homeodomain ZFHD1 and NAC transcription factors enhances expression of the ERD1 gene in *Arabidopsis*", Plant J., Jan. 2007;49(1):46-63.
Chen et al., "GmDREB2, a soybean DRE-binding transcription factor, conferred drought and high-salt tolerance in transgenic plants", Biochem Biophys Res Commun, Feb. 9, 2007;353(2):299-305.
Galen et al., "Functional ecology of a blue light photoreceptor: effects of phototropin-1 on root growth enhance drought tolerance in *Arabidopsis thaliana*", New Phytol, 2007;173(1):91-9.
Hong et al., "Heterologous expression of the AtDREB1A gene in chrysanthemum increases drought and salt stress tolerance", Sci China C Life Sci. Oct. 2006;49(5):436-45.
Quan et al., "Engineering of enhanced glycine betaine synthesis improves drought tolerance in maize", Plant Biotechnol, Nov. 2004; 2(6):477-86.
Fu et al., "Overexpression of barley hva1 gene in creeping bentgrass for improving drought tolerance", Apr. 2007;26(4):467-77.
Zhang et al., "Modulated fatty acid desaturation via overexpression of two distinct omega-3 desaturatases differently alters tolerance to various abiotic stresses in transgenic tobacco cells and plants", Plant J., Nov. 2005;44(3):361-71.
Suzuki et al., "Enhanced tolerance to environmental stress in transgenic plants expressing the transcriptional coactivator multiprotein bridging factor 1c", Plant Physiol., Nov. 2005;139(3):1313-22.
Dezar et al., "Hahb-4, a sunflower homeobox-leucine zipper gene, is a developmental regulator and confers drought tolerance to *Arabidopsis thaliana* plants", Transgenic Res., Aug. 2005;14(4):429-40.

(Continued)

*Primary Examiner*—Phuong T Bui
*Assistant Examiner*—Vinod Kumar
(74) *Attorney, Agent, or Firm*—Birch Stewart Kolasch & Birch, LLP

(57) ABSTRACT

The present invention is directed to drought responsive promoter sequences, polynucleotide constructs comprising the drought responsive promoters and methods of identifying the drought responsive promoters or fragments thereof. The invention further relates to the use of the present drought responsive promoters to modulate transcript levels.

12 Claims, No Drawings

OTHER PUBLICATIONS

Zhang et al., "Overexpression of WXP1, a putative Medicago truncatula AP2 domain-containing transcription factor gene, increases cuticular wax accumulation and enhances drought tolerance in transgenic alfalfa (Medicago sativa)", Plant J., Jun. 2005;42(5):689-707.

Zhang et al., "Expressing TERF1 in tobacco enhances drought tolerance and abscisic acid sensitivity during seedling development", Planta, Oct. 2005;222(3):494-501.

Wang et al., "Enhanced drought tolerance of transgenic rice plants expressing a pea manganese superoxide dismutase", J. Plant Physiol, Apr. 2005;162(4):465-72.

Oh et al., "*Arabidopsis* CBF3/DREB1A and ABF3 in transgenic rice increased tolerance to abiotic stress without stunting growth", Plant Physiol., May 2005;138(1):341-51.

Kim et al., "CAZFP1, Cys2/His2-type zinc-finger transcription factor gene functions as a pathogen-induced early-defense gene in Capsicum annuum", Plant Mol. Biol., Aug. 2004;55(6):883-904.

De Ronde et al., "Photosynthetic response of transgenic soybean plants, containing an Arabidopsis P5CR gene, during heat and drought stress", J Plant Physiol, Nov. 2004;161(11):1211-24.

Umezawa et al., "SRK2C, a SNF1-related protein kinase 2, improves drought tolerance by controlling stress-responsive gene expressionin *Arabidopsis thaliana*", Proc Natl Acad Sci USA, Dec. 7, 2004;101(49):17306-11.

Yan et al., "Overexpression of the *Arabidopsis* 14-3-3 protein GF14 lambda in cotton leads to a 'stay-green' phenotype and improves stress tolerance under moderate drought conditions", Plant cell Physiol., Aug. 2004;45(8):1007-14.

Kasukabe et al., "Overexpression of spermidine synthase enhances tolerance to multiple environmental stresses and up-regulates the expression of various stress-regulated genes in transgenic *Arabidopsis thaliana*", Plant Cell Physiol., Jun. 2004;45(6):712-22.

\* cited by examiner

SEQUENCE LISTING

```
<160> NUMBER OF SEQ ID NOS: 3

<210> SEQ ID NO 1
<211> LENGTH: 1097
<212> TYPE: DNA
<213> ORGANISM: Arabidopsis thaliana
<220> FEATURE:
<221> NAME/KEY: misc_feature
<222> LOCATION: (1)..(1097)
<223> OTHER INFORMATION: Construct PT0505 from Report Number 134

<400> SEQUENCE: 1
agtcgattgg cccgatcggc cagtctacga accggcttgc gcagtccact taccataaca      60
ggcagtatta gagtgggata tttgtaaatt gaggaagtca ctgcctcact ggtgacagta     120
ctttgtagat acctttcttt aattggttct gatgtgtttg gaattgtttg tttggaagga     180
tttgataaca aataaaatac aagcaaaaaa aaaaagata tggtcagaac tcagaaggca     240
acacaacgaa taggttgccg agtggggctc atgccgttga ttcttctgct cactgcccct     300
tctcctgtct attcacttcc tttgtccctt attttatct ttatttttgg tggtgaaaat      360
ttatgtttca tttatacaag ctaaaatgtt tttgttataa gtcaaacaaa aacaattatt     420
```

```
attaataata ttggaggctt ttattgtact tttggtttga aattttcgaa actacgtctc      480
ttaattctca tcctttgata ttctgtgcaa atgaatattt attttccata tagatagata      540 ttatttttt tgttggataa catttacact ttacccaaac ttgtaaacat gatttcacca       600
aaaaaaagct tgtaaacttg aatggaaaaa aatcagagta tataaaagat agtcttaaaa      660
ttggacaatg aagtaaatgt ggccctcaat atccggcatt tgcaagcaaa tcataccatc      720
tacatgtata tatactaaaa tgaaatgctt tattaggaag gaaatctttg aacagaaaaa      780
tagaaataag gtaagacaag aaaaaataac aatgaattac aatccacaaa tcccaagaat      840
gagaaaattt ttaatttcct aaagaatatt ttgacacgaa ttcgacatgt ataagataaa      900
actattaatt atttcagacg cctatatata accaccataa ctcttactct gttaccacca      960
caaagacaaa acaaaaaaaa agaggaagca attactatag gggaaaaaaa aatctgaaca     1020
aggcctgcag ggccagtgca ctgggatcca acaatgtcct ccgactcgtc caagatcaag     1080
aggaagcgga accgcat                                                    1097

<210> SEQ ID NO 2
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Construct PT0561 from Report Number 159

<400> SEQUENCE: 2
cgggctatac tggacttttg caaaaatgtg gttttatat tttatattgt attaggtttc        60
tgttaaaatt aaatgagaat tttaattaaa aagagaaatt atttgttaaa aaaaatcagg      120 atgggtcct aattattata tgttttgatt ttctatgaga aagttgcacc gtccattgtt       180
tcttgaaaac tattatctga ctaaaagaac agaaaatgta aagaaaagac aaagagacac      240
agagacgact ctgttaaata actctatagc agagtctctc gagttaaatc aataaaataa      300
agacctgaaa acatatattt cttcgaagca gtgtctaaaa ccaatgtaca atttatgaca      360
aaaggaacat gttatttag tcgcatataa ttacaaaata atcgcatgat ttatctaagt       420
tggtctttat taactcttaa caaaaaatta atataagaaa acagagtcag atttaaaaa       480 ccacttaatt agtccttcaa gaacaattat caaaacctta ataatgtttt catccaataa      540
catcctcgaa gtctcctcta aatcattgga tccaacgaaa ttcatgttta tctaaactaa      600
ctcgaataaa gaaacgatta taataattgc acactatgaa aaatatcaga agcgtcatag      660
aaattgtcgg ctacctccat gcacggaacc ttcacgaaac agttggtccc tcacacactt      720
catcgccacg ctataccacg tgtcaatttt acatacacca aaacatatct actaatcata      780
cctcttcacg tgtaacaaag tcccattcaa cgtggcaatt acagacccca aaattatgaa      840
ctaatcaaac ctcttcacgt gtcgcaaact tgtgaacgt tgaaaccccc cactcacacg       900
aagtgtatat atcctcttca caacacaaac ataaacatta cttcaaacaa agacttgaaa      960
gaactatctt tgttttcact catatcttat ctttattaaa                          1000

<210> SEQ ID NO 3
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Construct PT0688 from Report 183
```

```
<400> SEQUENCE: 3
acgttcagag gcatcgcttt tgtacaaatt gaagcgggtt tgttcaatat ttaaaataac      60
acaggaaaca ttcaaatgta ttattgatgt tgcttaggtt tgtgaaatga tatgaaccat     120
atcgtatata ttactagatt tttcttatat gttttaaggg tagtggggct gacctatcat     180
tctgtttggc attaccaatc agactatcag agtattcacc attcaggatt ccataactag     240
aaaaagaagg ggtttacatt ttctcatact gtataattt ctactatcag agattttatc      300
gattacatta atctcatagt gattattctg atttataaaa aagttgacaa ataattaaa      360 accagtattt tataacaaga ttgtctctct cccatggcca ttattttgac ctctgactta     420
tttaaatctt aattaacagc ataatactgt attaagcgta tttaaatgaa acaaaataaa     480
agaaaaaaag aacaaaacga aagagtggac cacatgcgtg tcaagaaagg ccggtcgtta     540
ccgttaaggt gtgtcgaact gtgattgggc cacgttaacg gcgtatccaa aagaaagaaa     600
gggcacgtgt atagatctag gaaaaaagaa agaatggacg gtttagattg tatctaggta     660
ccaggaaatg gaacgtcaca ccaaacggta cgtgtcggat cctgcccgtt gatgctgacg     720
gtcagcaact tccccttatt catgccccc tgcccgttaa ttacgtgtaa cccttccatg      780
cgaaaatcaa accctttttt ttttttgcgt tcttcttcaa cttttctttt taaatcaaac     840
cttttctttt taaatcaca ttgcatttcc taacgctcaa caaaatctct ctctactaat      900
atctctctct ctctctctct attgttgaag aagactcata atcggagatt gtttgttttt     960
ggtttgctct gtaaattgga gaagttttgt tagagatcaa                          1000
```

DROUGHT INDUCIBLE PROMOTERS AND USES THEREOF

This Nonprovisional application claims priority under 35 U.S.C. § 119(e) on U.S. Provisional Application No(s). 60/637,269 filed on Dec. 16, 2004, the entire contents of which are hereby incorporated by reference.

FIELD OF THE INVENTION

The present invention relates to drought responsive promoters that are useful for modulating transcription of a desired polynucleotide. Such drought responsive promoters can be included in a polynucleotide construct, expression cassette or vector, or inserted into the chromosome or used as an exogenous element to modulate in vivo and in vitro transcription of a polynucleotide. The invention also includes host cells and organisms, including plant cells and regenerated plants therefrom, with desired traits or characteristics obtained using polynucleotides comprising the drought responsive promoters of the present invention.

BACKGROUND OF THE INVENTION

Plants are constantly exposed to a variety of biotic (e.g., pathogen infection and insect herbivory) and abiotic (e.g., high or low temperature, drought, flood, anaerobic conditions and salinity) stresses. To survive these challenges, plants have developed elaborate mechanisms to perceive external signals and to manifest adaptive responses with proper physiological and morphological changes (Bohnert et al., 1995). Plants exposed to heat and/or low water or drought conditions typically have low yields of plant material, seeds, fruit and other edible products. Practically all agricultural regions are prone to drought due to climatic variation or socio-economic constraints on water resources. It would, therefore, be of great interest and importance to be able to identify genes that confer drought tolerance to thereby enable one to create transformed plants (such as crop plants) with improved ability to survive water limiting conditions.

Plants cannot grow without sufficient water. While nutrient availability plays a critical role in plant growth and development, these nutrients must be in aqueous form. In addition, many marginal growing regions may have an adequate nutrient supply, but without enough water to allow maintenance of plant turgor and membrane integrity, such lands cannot be maximally cultivated. Increased plant drought tolerance enables the production of higher yields from such lands and/or enables existing yields of crops to be obtained with lower water input. As a consequence, crops are produced more cost-effectively.

One of the major consequences of drought is the loss of water from the protoplasm, which leads to increased ion concentrations within the cell. At high concentrations ions such as chlorine and nitrate inhibit metabolic functions (Hartung et al (1998) Prog Bot 59:299-327).Eventually a "glassy state" results from cell water loss and the concentration of protoplasmic constituents. Here, the remaining cell liquid is highly viscous, which increases the chances of protein denaturation and membrane fusion due to abnormal molecular interactions (see: Hartung et al. (1998) Prog Bot 59:299-327 and Hoekstra et al. (2001) Trends Plant Sci 6:431-438).This indicates that the ability to maintain cell turgor and metabolism is genetically encoded.

In the field of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Availability and maintenance of a reproducible stream of food and feed has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed and energy for the population.

SUMMARY OF THE INVENTION

The present invention is directed to isolated polynucleotide sequences that comprise drought responsive promoters from *Arabidopsis thaliana* used alone or in combination with other promoters, promoter control elements and motifs functional in plants.

It is an object of the present invention to provide isolated polynucleotides that are drought responsive promoter sequences. These promoter sequences comprise, for example, (1) a polynucleotide having a nucleotide sequence according to any one of the promoter sequences set forth in Table 1 (SEQ ID NOs: 1-3) or a functional fragment thereof;

(2) a polynucleotide having a nucleotide sequence with at least 80% sequence identity to any one of the promoter sequences set forth in Table 1 (SEQ ID NOs: 1-3) or a functional fragment thereof; and (3) a polynucleotide having a nucleotide sequence which hybridizes to any one of the promoter sequences set forth in Table 1 (SEQ ID NOs: 1-3) under a condition establishing at least a Tm-20° C.

Drought responsive promoters drive transcription in response to drought conditions. Drought responsive promoter can drive expression in a number of different plant tissues, for example root tissue (e.g., root endodermis, root epidermis or root vascular tissues).

In another embodiment, the present drought responsive promoters are capable of serving as or fulfilling the function of a core promoter, an initiator site, a transcription factor binding site, an enhancer, an inverted repeat, a locus control region, or a scaffold/matrix attachment region.

In another embodiment, the present isolated polynucleotides comprise a drought responsive promoter as described above, wherein the promoter is operably linked to a polynucleotide to be transcribed.

In another embodiment of the present invention, the drought responsive promoters of the instant invention are operably linked to a heterologous polynucleotide that is a coding sequence or that is a regulatory sequence.

The present invention further embodies a vector comprising a first nucleic acid having a nucleotide sequence encoding a plant transcription and/or translation signal, and a second nucleic acid having a nucleotide sequence according to the isolated nucleic acid molecules of the present invention. More particularly, the first and second nucleic acids may be operably linked. Even more particularly, the second nucleic acid may be endogenous to a first organism, and any other nucleic acid in the vector may be endogenous to a second organism. Most particularly, the first and second organisms may be from different species.

It is another object of the present invention to provide a host cell comprising an isolated polynucleotide or vector as described above or fragment thereof. Host cells include bacterial, yeast, insect, mammalian and plant. Such a drought responsive promoter can modulate transcription of a sequence in cis- and/or in trans-.

In yet another embodiment, the present host cell is a plant cell capable of regenerating into a plant.

It is yet another embodiment of the present invention to provide a plant comprising an isolated polynucleotide or vector described above.

It is another object of the present invention to provide a method of modulating transcription in a sample that contains either a cell-free transcription system or a host cell. This method comprises providing a polynucleotide or vector according to the present invention as described above and contacting the sample of the polynucleotide or vector with conditions that permit transcription.

In another embodiment of the present method, the polynucleotide or vector preferentially modulates root growth, tolerance to pests, and soil interactions.

In another embodiment of the present method, the polynucleotide or vector preferentially modulates root composition for human food or animal feed applications.

The present invention also provides a method of obtaining an enhanced plant with a drought responsive promoter selected from Table 1 (SEQ ID NOs: 1-3).

The present invention also provides an enhanced plant with a drought responsive promoter selected from Table 1 (SEQ ID NOs: 1-3).

Other and further objects of the present invention will be made clear or become apparent from the following description.

DETAILED DESCRIPTION OF THE INVENTION

1. Definitions

The following terms are utilized throughout this application:

Drought: Plant species vary in their capacity to tolerate drought conditions. "Drought" can be defined as the set of environmental conditions under which a plant will begin to suffer the effects of water deprivation, such as decreased stomatal conductance and photosynthesis, decreased growth rate, loss of turgor (wilting), or ovule abortion. For these reasons, plants experiencing drought stress typically exhibit a significant reduction in biomass and yield. Water deprivation may be caused by lack of rainfall or limited irrigation. Alternatively, water deficit may also be caused by high temperatures, low humidity, saline soils, freezing temperatures or water-logged soils that damage roots and limit water uptake to the shoot. Since plant species vary in their capacity to tolerate water deficit, the precise environmental conditions that cause drought stress can not be generalized. However, drought tolerant plants produce higher biomass and yield than plants that are not drought tolerant under water limited conditions and may also exhibit enhanced survivability and/or delayed desiccation under severely water limited conditions. Differences in physical appearance, recovery and yield can be quantified and statistically analyzed using well known measurement and analysis methods.

Drought Responsive Promoters or Drought Inducible Promoters: Drought responsive promoters drive transcription in response to drought conditions (see definition of "drought" above). Drought responsive promoters can drive expression in a number of different plant tissues including, but not limited to, root tissue (e.g., root endodermis, root epidermis, or root vascular tissues) and leaf tissue (e.g. epidermis, mesophyll or leaf vascular tissue). Drought responsive promoters may also drive transcription in response to heat and/or ABA.

Flood: Plant species vary in their capacity to tolerate flooding. Some plants, such as rice, are cultivated in water while plants such as corn do not tolerate flooding. "Flood," as referred to within, is the state of water saturation at which soils become hypoxic or anoxic, thus limiting respiration in the root. Reduced respiration damages roots and can limit the permeability of roots to water, resulting in decreased leaf water potential and wilting. Since plant species vary in their capacity to tolerate flooding, the precise environmental conditions that cause flood stress can not be generalized. However, flood tolerant plants are characterized by their ability to retain their normal appearance or recover quickly from flood. Such flood tolerant plants produce higher biomass and yield than plants that are not flood tolerant. Differences in physical appearance, recovery and yield can be quantified and statistically analyzed using well known measurement and analysis methods.

Functionally Comparable Proteins or Functional Homologs: This term describes those proteins that have at least one functional characteristic in common. Such characteristics include sequence similarity, biochemical activity, transcriptional pattern similarity and phenotypic activity. Typically, the functionally comparable proteins share some sequence similarity or at least one biochemical property. Within this definition, homologs, orthologs and analogs are considered to be functionally comparable. In addition, functionally comparable proteins generally share at least one biochemical and/or phenotypic activity.

Functional homologs will give rise to the same characteristic to a similar protein, but not necessarily to the same, degree. Typically, functional homologs give the same characteristics where the percent sequence identity of one of the comparables is at least 20% of the other; more typically, between 30 to 40%; even more typically, between 50%-60%; even more typically 70% to 80%; even more typically between 90% to 100% of the other.

Functionally Comparable Promoters or Functionally Similar Promoters: As used herein, "Functionally Comparable Promoters" or "Functionally Similar Promoters" are promoters that drive genes encoding functional homologs having similar expression patterns. Functionally comparable promoters may share sequence identity. Functionally comparable promoters may be isolated from the same plant species or different plant species. Such promoters include both naturally occurring promoters and non-natural promoter sequences. Non-natural functionally similar promoters include synthetic or modified natural promoters with nucleotide substitutions, insertions, deletions or fragments of naturally-occurring promoter sequences that do not substantially affect transcription modulation activity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

High Temperature: Plant species vary in their capacity to tolerate high temperatures. Very few plant species can survive temperatures higher than 45° C. The effects of high temperatures on plants, however, can begin at lower temperatures depending on the species and other environmental conditions such as humidity and soil moisture. "High temperature" can be defined as the temperature at which a given plant species will be adversely affected as evidenced by symptoms such as decreased photosynthesis. Since plant species vary in their capacity to tolerate high temperature, the precise environmental conditions that cause high temperature stress can not be generalized. However, high temperature tolerant plants are characterized by their ability to retain their normal appearance or recover quickly from high temperature conditions. Such high temperature tolerant plants produce higher biomass and yield than plants that are not high temperature tolerant. Differences in physical appearance, recovery and yield can be quantified and statistically analyzed using well known measurement and analysis methods.

Low Temperature: Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "low temperature" can be defined as the temperature at which a given plant species will be adversely affected as evidenced by symptoms such as decreased photosynthesis and membrane damage (measured by electrolyte leakage). Since plant species vary in their capacity to tolerate low temperature, the precise environmental conditions that cause low temperature stress can not be generalized. However, low temperature tolerant plants are characterized by their ability to retain their normal appearance or recover quickly from low temperature conditions. Such low temperature tolerant plants produce higher biomass and yield than plants that are not low temperature tolerant. Differences in physical appearance, recovery and yield can be quantified and statistically analyzed using well known measurement and analysis methods.

Plant seeds vary considerably in their ability to germinate under low temperature conditions. Seeds of most plant species will not germinate at temperatures less than 10° C. Once seeds have imbibed water they become very susceptible to disease, water and chemical damage. Seeds that are tolerant to low temperature stress during germination can survive for relatively long periods under which the temperature is too low to germinate. Since plant species vary in their capacity to tolerate low temperature during germination, the precise environmental conditions that cause low temperature stress during germination can not be generalized. However, plants that tolerate low temperature during germination are characterized by their ability to remain viable or recover quickly from low temperature conditions. Such low temperature tolerant plants produce, germinate, become established, grow more quickly and ultimately produce more biomass and yield than plants that are not low temperature tolerant. Differences in germination rate, appearance, recovery and yield can be quantified and statistically analyzed using well known measurement and analysis methods.

Percentage of sequence identity: As used herein, the term "percent sequence identity" refers to the degree of identity between any given query sequence and a subject sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site and at the European Bioinformatics Institute site, both available on the World Wide Web via the internet.

In case of the functional homolog searches, to ensure a subject sequence having the same function as the query sequence, the alignment has to be along at least 80% of the length of the query sequence so that the majority of the query sequence is covered by the subject sequence.

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Plant Tissue: The term "plant tissue" includes differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Regulatory regions can be classified in two categories, promoters and other regulatory regions.

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m = 81.5 - 16.6(\log_{10}[Na^+]) + 0.41(\%G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log\{[Na^+]/(1+0.7[Na^+])\} + 0.41(\%G+C) - 500/L \; 0.63(\%\text{fomamide}) \quad (2)$$

where L is the length of the probe in the hybrid. (P. Tijessen, "Hybridization with Nucleic Acid Probes" In Laboratory Techniques in Biochemistry and Molecular Biology, vand der Vliet, ed., c. 1993 by Elsevier, Amsterdam, which is hereby incorporated by reference in its entirety). The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al. (1973) J. Mol. Biol. 81:123), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

TATA to start: "TATA to start" shall mean the distance, in number of nucleotides, between the primary TATA motif and the start of transcription.

Transformation: Examples of means by which this can be accomplished are described below and include *Agrobacterium*-mediated transformation (of dicots (9-10), of monocots (11-13), and biolistic methods (14)), electroporation, inplanta techniques, and the like. Such a plant containing the exogenous nucleic acid is referred to here as a $T_0$ for the primary transgenic plant and $T_1$ for the first generation.

$T_0$: As used in the current application, the term "$T_0$" refers to the whole plant, explant or callus tissue inoculated with the transformation medium and used to generate all events for a particular nucleotide sequence.

$T_1$: As used in the current application, the term $T_1$ refers to a unique event which is either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

2. Introduction

The polynucleotides of the invention comprise drought responsive promoters that are capable of modulating transcription in response to developmental or varying soil conditions, thereby enhancing the ability of a plant to grow under such conditions.

Such drought responsive promoters can be used in combination with native or heterologous promoter fragments, control elements or other regulatory sequences to modulate transcription and/or translation.

Specifically, drought responsive promoters of the invention can be used to modulate transcription of a desired polynucleotide, which include without limitation:

(a) antisense;
(b) RNAi;
(c) ribozymes;
(d) coding sequences; or
(e) fragments thereof.

The drought responsive promoter also can modulate transcription in a host genome in cis- or in trans-.

In an organism such as a plant, the drought responsive promoters of the instant invention are useful to produce preferential transcription which results in a desired pattern of transcript levels in a particular cell, tissue or organ, or under particular conditions.

3. Description of the Invention, Experimental Procedures and Results.

A. Identifying and Isolating Promoter Sequences of the Invention

The drought responsive promoters of the present invention are presented in Table 1 (SEQ ID NOs: 1-3). Additional promoter sequences encompassed by the invention can be identified as described below.

The effects of substitutions, insertions and deletions to the drought responsive promoter sequences may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

(1) Cloning Methods

Isolation from genomic libraries of polynucleotides comprising the sequences of the drought responsive promoters of the present invention is possible using known techniques.

For example, polymerase chain reaction (PCR) can amplify the desired polynucleotides using primers designed from sequences in the row titled "The spatial expression of the promoter-marker-vector". Polynucleotide libraries comprising genomic sequences can be constructed according to Sambrook et al. (1989) In Molecular Cloning: A Laboratory Manual, $2^{nd}$ Ed. Cold Spring Harbor Press, Cold Spring Harbor, N.Y., which is hereby incorporated by reference in its entirety), for example.

Other procedures for isolating polynucleotides comprising the drought responsive promoters sequences of the invention include, without limitation, tail-PCR and 5' rapid amplification of cDNA ends (RACE). See, for tail-PCR, for example, Liu et al. (1995 Plant J 8(3): 457-463); Liu et al. (1995) Genomics 25: 674-681; Liu et al. (1993) Nucl. Acids Res. 21(14): 3333-3334; and Zoe et al. (1999) BioTechniques 27(2): 240-24; for RACE, see, for example, PCR Protocols: A Guide to Methods and Applications, (1990) Academic Press, Inc. These publications are hereby incorporated by reference in their entirety.

(2) Chemical Synthesis

In addition, the drought responsive promoters of the invention can be chemically synthesized according to techniques in common use. See, for example, Beaucage et al. (1981) Tet Lett 22: 1859 and U.S. Pat. No. 4,668,777.

Such chemical oligonucleotide synthesis can be carried out using commercially available devices, such as a Biosearch 4600 or 8600 DNA synthesizer (Applied Biosystems, a division of Perkin-Elmer Corp., Foster City, Calif., USA) and an Expedite (Perceptive Biosystems, Framingham, Mass., USA).

Synthetic RNA, including natural and/or analog building blocks, can be synthesized on the Biosearch 8600 machines, see above.

Oligonucleotides can be synthesized and then ligated together to construct the desired polynucleotide.

B. Isolating Functionally Similar Promoters

Included in the present invention are drought responsive promoters exhibiting nucleotide sequence identity to those described in Table 1 (SEQ ID NOs: 1-3).

Naturally occurring drought responsive functionally similar promoters that exhibit nucleotide sequence identity to those shown in Table 1 (SEQ ID NOs: 1-3) can be isolated using the techniques as described above. More specifically, such promoters can be identified by varying stringencies, as defined above, in typical hybridization procedures such as Southern blots or probing of polynucleotide libraries, for example.

Naturally occurring drought responsive functionally similar promoters that do not exhibit nucleotide sequence identity to those shown in Table 1 (SEQ ID NOs: 1-3) can be isolated using the techniques as described above. More specifically, functional homologs are identified and their expression patterns compared to identify functional homologs with similar expression patterns. The promoters from these functional homologs can then be isolated as described above.

Non-natural drought responsive promoter variants of those shown in Table 1 (SEQ ID NOs: 1-3) can be constructed using cloning methods that incorporate the desired nucleotide variation. See, for example, Ho et al. (1989) Gene 77:51-59, describing a procedure site directed mutagenesis using PCR.

Testing of Polynucleotides

Polynucleotides of the invention are tested for activity by cloning the sequence into an appropriate vector, transforming plants with the construct and assaying for marker gene expression. Recombinant DNA constructs are prepared which comprise the polynucleotide sequences of the invention inserted into a vector suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al. (1992) Proc. Natl. Acad. Sci. USA 89: 8794-8797; Hamilton et al. (1996) Proc. Natl. Acad. Sci. USA 93: 9975-9979;

(b) YAC: Burke et al. (1987) Science 236:806-812;

(c) PAC: Sternberg et al. (1990) Proc Natl Acad Sci U S A. Jan;87(1):103-7;

(d) Bacteria-Yeast Shuttle Vectors: Bradshaw et al. (1995) Nucl Acids Res 23: 4850-4856;

(e) Lambda Phage Vectors: Replacement Vector, e.g., Frischauf et al. (1983)J. Mol Biol 170: 827-842; or Insertion vector, e.g., Huynh et al. (1985) In DNA Cloning: A practical Approach, Vol. 1, Glover ed., Oxford: IRL Press; T-DNA gene fusion vectors :Walden et al. (1990) Mol Cell Biol 1: 175-194; and (g) Plasmid vectors: Sambrook et al., infra.

Typically, the construct comprises a vector containing a sequence of the present invention operably linked to any marker gene. The polynucleotide is identified as a drought responsive promoter by the expression of the marker gene under appropriate conditions. Many marker genes can be used including Green Fluorescent Protein (GFP), GUS, YFP, etc. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron, glyphosate or phosphinotricin. Vectors can also include origins of replication, scaffold attachment regions (SARs), markers, homologous sequences, introns, etc.

A general description of expression vectors and reporter genes can be found in Gruber, et al. (1993) Vectors for Plant Transformation In Methods in Plant Molecular Biology & Biotechnology, pp. 89-119, Glich et al. eds., CRC Press. Moreover GUS expression vectors and GUS gene cassettes are available from Clonetech Laboratories, Inc. (Palo Alto, Calif.) while luciferase expression vectors and luciferase gene cassettes are available from Promega Corp. (Madison, Wis.). GFP vectors are available from Aurora Biosciences.

C. Constructing Promoters with Control Elements (1) Combining Promoters and Promoter Control Elements The drought responsive promoter sequences of the present invention, can be combined with each other to produce the desired preferential transcription. Also, the polynucleotides of the invention can be combined with other known sequences to obtain other useful promoters to modulate, for example, tissue specific transcription or transcription specific to certain conditions. Such preferential transcription can be determined using the techniques or assays described above.

Fragments and variants, as well as the full-length sequences of those shown in Table 1 (SEQ ID NOs: 1-3) and relatives are useful alone or in combination.

It may also be useful to attach a marker sequence to the present drought responsive promoter in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al. (1985) Nature 317: 741-744; Gordon-Kamm et al. (1990) Plant Cell 2: 603-618; and Stalker et al. (1988) Science 242: 419423). Other marker genes exist which provide hormone responsiveness.

(1) Modification of Transcription by Drought Responsive Promoters

The drought responsive promoters of the present invention are operably linked to a polynucleotide to be transcribed. In this manner, the drought responsive promoter modifies transcription by modulating transcript levels of that polynucleotide when inserted into a genome.

However, prior to insertion into a genome, the drought responsive promoter need not be linked, operably or otherwise, to a polynucleotide to be transcribed. For example, the drought responsive promoter is inserted alone into the genome in front of a polynucleotide already present in the genome. In this manner, the drought responsive promoter modulates the transcription of a polynucleotide that was already present in the genome. This polynucleotide may be native to the genome or inserted at an earlier time.

Alternatively, the drought responsive promoter is inserted into a genome alone to modulate transcription. See, for example, Vaucheret et al. (1998) Plant J 16: 651-659. Rather, the drought responsive promoter is simply inserted into a genome or maintained extrachromosomally as a way to divert transcription resources of the system to itself. This approach may be used to down-regulate the transcript levels of a group of polynucleotides.

(2) Polynucleotide to be Transcribed

The nature of the polynucleotide to be transcribed is not limited. Specifically, the polynucleotide includes sequences that have activity as RNA as well as sequences that result in a polypeptide product. These sequences include, but are not limited to, antisense sequences, RNAi sequences, ribozyme sequences, spliceosomes, amino acid coding sequences and fragments thereof.

Specific coding sequences may include, but are not limited to endogenous proteins or fragments thereof, or heterologous proteins including marker genes or fragments thereof.

Drought responsive promoters of the present invention are useful for modulating metabolic or catabolic processes. Such processes include, but are not limited to, water uptake, turgor control and maintenance of membrane integrity. Some examples of genes, transcripts and peptides or polypeptides participating in these processes, which can be modulated by the present invention are: 9-cis-epoxycarotenoid (NCED), zeaxanthin epoxidase gene, abg1, ERD5 (early responsive to dehydration) and aquaporin genes such as PIP2 or ZmPIP (plasma membrane intrinsic protein). Alternatively, expression constructs are used to inhibit expression of genes or peptides and polypeptides involved in ABA degradation by incorporating the drought promoters in constructs for antisense use, co-suppression use, RNA interference use or for the production of dominant negative mutations.

F. Insertion of Polynucleotide and Vectors Into A Host Cell

The polynucleotides according to the present invention can be inserted into a host cell. A host cell includes but is not limited to a plant, mammalian, insect, yeast and prokaryotic cell, preferably a plant cell.

The method of insertion into the host cell genome is chosen based on convenience. For example, the insertion into the host cell genome may be accomplished either by vectors that integrate into the host cell genome or by vectors which exist independent of the host cell genome (1) Polynucleotides Autonomous of the Host Genome The polynucleotides of the present invention exist autonomously or independent of the host cell genome. Vectors of these types are known in the art and include, for example, certain types of non-integrating viral vectors, autonomously replicating plasmids, artificial chromosomes and the like.

Additionally, in some cases transient expression of a polynucleotide is desired.

(2) Polynucleotides Integrated into the Host Genome

The drought responsive promoters of the present invention may be transformed into host cells. These transformations may be into protoplasts or intact tissues or isolated cells. Preferably expression vectors are introduced into intact tissue. General methods of culturing plant tissues are provided for example by Maki et al. (1993) Procedures for Introducing Foreign DNA into Plants In Methods in Plant Molecular Biology & Biotechnology, pp. 67-88, Glich et al. eds., CRC Press CRC; and by Phillips et al. (1988) Cell-Tissue Culture and In-Vitro Manipulation In Corn & Corn Improvement, 3rd Edition 10, pp. 345-387, Sprague et al. eds, American Society of Agronomy Inc.

Methods of introducing polynucleotides into plant tissue include the direct infection or co-cultivation of a plant cell with *Agrobacterium tumefaciens* (Horsch et al. (1985) Science 227:1229). Descriptions of *Agrobacterium* vector systems and methods for *Agrobacterium*-mediated gene transfer provided by Gruber et al. supra.

Alternatively, polynucleotides are introduced into plant cells or other plant tissues using a direct gene transfer method such as microprojectile-mediated delivery, DNA injection, electroporation and the like. More preferably polynucleotides are introduced into plant tissues using the microprojectile media delivery with the biolistic device. See, for example, Tomes et al. (1995) Direct DNA transfer into intact plant cells via microprojectile bombardment In Plant Cell, Tissue and Organ Culture: Fundamental Methods, Gamborg and Phillips eds., Springer Verlag, Berlin.

In another embodiment of the current invention, expression constructs are used for gene expression in callus culture for the purpose of expressing marker genes encoding peptides or polypeptides that allow identification of transformed plants. Here, a drought responsive promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells are transferred to callus shoot-inducing or callus root-inducing media. Gene expression occurs in the callus cells developing on the appropriate media: callus root-inducing promoters will be activated on callus root-inducing media, etc.

Examples of such peptides or polypeptides useful as transformation markers include, but are not limited to, barstar, glyphosate, chloramphenicol acetyltransferase (CAT), kanamycin, spectinomycin, streptomycin or other antibiotic resistance enzymes, green fluorescent protein (GFP), β-glucuronidase (GUS), etc. Some of the exemplary drought responsive promoters of Table 1 (SEQ ID NOs: 1-3) will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art, for example, by the homologous sequences or T-DNA discussed above or using the cre-lox system (Vergunst et al. (1998) Plant Mol. Biol. 38:393).

G. Using the Promoters of the Invention (1) Common Uses

In yet another embodiment, the drought responsive promoters of the present invention are used to further understand developmental mechanisms. For example, drought responsive promoters that are specifically induced during callus, somatic embryo, shoot or root formation are used to explore the effects of overexpression, repression or ectopic expression of target genes or for isolation of trans-acting factors.

The vectors of the invention are used not only for expressing coding regions, but also in exon-trap cloning or promoter trap procedures to detect differential gene expression in various tissues (Lindsey et al. (1993) Transgenic Research 2:3347; Auch & Reth, et al. Nucleic Acids Research 18(22): 674, Nov. 25 1990).

Entrapment vectors, first described for use in bacteria (Casadaban and Cohen (1979) Proc Nat Aca Sci USA 76: 4530; Casadaban et al. (1980) J. Bacteriol 143: 971) permit selection of insertional events that lie within coding sequences. Entrapment vectors are introduced into pluripotent ES cells in culture and then passed into the germline via chimeras (Gossler et al. (1989) Science 244: 463; Skarnes (1990) Biotechnology 8: 827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene coupled to a reporter gene. The DNA constructs are inserted into a bacterial strain otherwise lacking the metabolic gene, and the resulting bacteria are used to infect the host organism. Only bacteria expressing the metabolic gene survive in the host organism; consequently, inactive constructs can be eliminated by harvesting only bacteria that survive for some minimum period in the host. At the same time, constitutively active constructs can be eliminated by screening only bacteria that do not express the reporter gene under laboratory conditions. The bacteria selected by such a method contain constructs that are selectively induced only during infection of the host. The IVET approach can be modified for use in plants to identify genes induced in either the bacteria or the plant cells upon pathogen infection or root colonization. For information on IVET see the articles by Mahan et al. (1993) in Science 259:686-688, Mahan et al. (1995) in PNAS USA 92:669-673, Heithoff et al. (1997) in PNAS USA 94:934-939 and Wang et al. (1996) in PNAS USA. 93:10434.

(2) Particular Uses

Nutrient availability is arguably the rate-limiting element in plant growth and all field crops have a fundamental dependence on exogenous nutrient sources to a greater or lesser degree. Increased efficiency of nutrient use by plants enables the production of higher yields with existing fertilizer inputs and/or enables existing yields of crops to be obtained with lower fertilizer input or enables better yields on soils of poorer quality. Also, higher amounts of proteins in the crops are produced more cost-effectively.

Drought responsive promoter sequences are used in combination with gene coding sequences, either gDNA or cDNA, to induce the expression of proteins and enzymes during conditions of low soil or solution nutrient concentration. Increased mRNA expression via one of the drought responsive promoters described herein is used to overcome rate limiting steps in nutrient assimilation, transport and metabolism. General reviews of some of these processes can be found in: Derlot. et al. (2001) Amino Acid Transport In Plant Nitrogen, pp. 167-212, Lea and Morot-Gaudry eds., Springer-Verlag, Berlin, Heidelberg; Glass et al. (2002) J. Exp. Bot. 53: 855-864, Krapp et al. (2002) Nitrogen and Signaling. In Photosynthetic Nitrogen Assimilation and Associated Carbon Respiratory Metabolism, pp. 205-225, Foyer and Noctor eds., Kluwer Academic Publisher, Dordrecht, The Netherlands; and Touraine et al. (2001) Nitrate uptake and its regulation. In Plant Nitrogen, pp. 1-36, Lea and Morot-Gaudry eds, Springer-Verlag, Berlin, Heidelberg.

The promoter of the invention can be used to modulate transcription of a polynucleotide to confer desired characteristics to a plant. The polynucleotides to be so modulated can be:

(a) polynucleotides that confer resistance or tolerance to insects, nematodes, fungi, bacteria, viruses, seed as those that code for *Bacillus thuringiensis* (Bt) insecticidal protein;

(b) polynucleotides that confer increased biomass, higher seed yield, reduced nitrogen seeds, faster rate of growth or faster seedling growth, such as those described in co-pending application Ser. No. 11/298,391, filed on Dec. 8, 2005 entitled "Nucleotide Sequences and Corresponding Polypeptides Conferring Modulated Plant Size and Biomass in Plants"; and (c) polynucleotides that confer enhanced water uptake, turgor control and maintenance of membrane integrity, such as those described in co-pending U.S. application Ser. No. 11/305,666 filed on Dec. 15, 2005 entitled "Nucleotide Sequences and Corresponding Polypeptides Encoded Thereby Useful for Enhancing Plant Drought Tolerance" and Ser. No. 11/228,587 filed Sep. 16, 2005.

Drought responsive promoters are also used to turn off the expression of genes that are not beneficial to root development and nutrient uptake, use and/or transport. Here, the drought responsive promoter is operably linked to the antisense orientation of a non-beneficial gene sequence. Expression of this antisense gene sequence has the effect of decreasing the amount of the non-beneficial sequence such that the expression of the protein encoded by the non-beneficial sequence is reduced. The reduction in expression of the non-beneficial sequence leads to a reduction in the genetic function of the protein, thus allowing for more efficient development and nutrient uptake, utilization and transport (Hamada et al. (1996) Transgenic Res 5: 115-121; Takahashi et al. (2001) Plant Physiol. 126: 731-741; Temple et al. (1998) Plant Mol Biol 37: 535-547).

Drought responsive promoters are further used to express a non-beneficial sequence in inverted orientation, thus producing a double stranded RNA molecule. Double stranded RNAs are recognized in plant cells as foreign and are targeted for degradation (Vance and Vaucheret (2001) Science 292: 2277-2280; Wesley et al. (2001) Plant J 27: 581-590.). The end result is reduced expression of the mRNA of the non-beneficial sequence, which leads to reduced gene function (Tang et al. (2003) Genes Dev 17: 49-63).

Another alternative consists in utilizing the promoters of the invention to inhibit expression of a drought responsive polypeptide in a plant species of interest. The term "expression" refers to the process of converting genetic information encoded in a polynucleotide into RNA through transcription of the polynucleotide (i.e., via the enzymatic action of an RNA polymerase), and into protein, through translation of mRNA. "Up-regulation" or "activation" refers to regulation that increases the production of expression products relative to basal or native states, while "down-regulation" or "repression" refers to regulation that decreases production relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a drought responsive polypeptide. A nucleic acid that decreases the level of a transcription or translation product of a gene encoding a drought responsive polypeptide is transcribed into an antisense nucleic acid similar or identical to the sense coding sequence of the drought responsive polypeptide. Alternatively, the transcription product of an isolated nucleic acid can be similar or identical to the sense coding sequence of a drought responsive polypeptide, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C, Humana Press Inc., Totowa, N.J. RNA endoribonucleases such as the one that occurs naturally in *Tetrahymena thermophila*, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering mRNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the drought responsive polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., 1996, *Bioorgan. Med. Chem.*, 4: 5-23. In addition, the deoxyphosphate backbone can be replaced with, for example, a phosphorothioate or phosphorodithioate backbone, a phosphoroamidite, or an alkyl phosphotriester backbone.

Drought promoter sequences are used in combination with gene coding sequences, either gDNA or cDNA, to induce the expression of proteins and enzymes during drought conditions. Increased MRNA expression via one of the drought promoters described herein is used to overcome rate limiting steps in water uptake, turgor maintenance and membrane integrity/maintenance. General reviews of some of these processes can be found in: Javot and Maurel (2002) Annals of Bot 90:301-313, Steudle (2000) Plt Soil 226:45-56, Wang and Smith (2004) Aust J Agric Res 55:501-523, Turner and Jones (1980) Turgor maintenance by osmotic adjustment: A review and evaluation. In *Adaptation of Plants to Water and High Temperature Stress*, N. C. Turner and P. J. Kramer, eds, Wiley, New Your, pp. 87-103, and Barkla and Pantoja (1996) Annu Rev Plant Physiol Plant Mol Biol 47:159-184.

Drought responsive promoters that are expressed in the root are used to modify root architecture by increasing or decreasing the expression of genes involved in primary and lateral root formation. For example the ANR1 gene is involved in nitrogen dependent lateral root formation (Zhang and Forde (2000) J. Exp. Bot 51: 51-59). Antisense inhibition of ANR1 gene expression results in a decrease in lateral root formation at inducing concentrations of nitrate (Zhang and Forde (1998) Science 279: 407-409.). Conversely, increased expression of ANR1 and other proteins involved in lateral root formation are used to increase lateral root number and length and thus increase nitrogen uptake from the soil or solution by increasing surface area contact between soil or solution and root absorbing surface.

The drought responsive promoters of the present invention are also useful for modulating uptake, use and metabolism of other nutrients. For example, the Sultr1 gene is a sulfate transporter while ADT1 is a potassium channel. The promoters of the invention are used to increase the expression of these gene products. These gene products modify the response of the plant to available sulfer and potassium.

The drought responsive promoters of the invention also down-regulate genes which lead to feedback inhibition, for example of nitrogen uptake and reduction. An example of such genes are those encoding the 14-3-3 proteins, which repress nitrate reductase (Swiedrych et al. (2002) J Agric Food Chem 27;50(7):2137-41. Here, the drought responsive promoters described herein are used to drive expression of an antisense copy of a 14-3-3 protein. The resulting transgenic plants have an increase in amino acid content and protein content in the seed and/or leaves. Such plants are especially useful for livestock feed. For example, an increase in amino acid and/or protein content in alfalfa provides an increase in forage quality and thus enhanced nutrition.

I. Experimental Procedures and Results

GFP Experimental Procedures and Results

Procedures

The polynucleotide sequences of the present invention are tested for promoter activity using Green Fluorescent Protein (GFP) assays in the following manner.

Approximately 1-2 kb of genomic sequence occurring immediately upstream of the ATG translational start site of the gene of interest is isolated using appropriate primers tailed with BstXI restriction sites. Standard PCR reactions using these primers and genomic DNA are conducted. The resulting product is isolated, cleaved with BstXI and cloned into the BstXI site of an appropriate vector.

Transformation

The following procedure is used for transformation of plants

1. Seed Preparation and Plant Growth.

A homogeneous mixture of *Arabidopsis thaliana* seed in a 0.2% Phytagar solution is inclubated at 4° C. in the dark for 3 days. Seed is planted in 4 inch pots in a soil miture of Sunshine Mix, Vermiculite, Marathon and Osmocote. Pots are placed in flats, covered with plastic domes and subsequently subirrigated. After 3 to 4 days, the domes are removed.

Seven to ten days after planting, seedlings are thinned to 20 plants per pot. When 5-10 cm long bolts appear, they are clipped between the first node and the stem base to induce secondary bolts. Six to 7 days after clipping, the plants are transformed via dipping infiltration.

2. Preparation of *Agrobacterium*.

Each 4 inch pot is inverted and the aerial portion of the plants submerged into a 16 oz. polypropylene container holding 200 mls of *Agrobacterium tumefaciens* ($1 \times 10^7$ bacteria) in Infiltration media (2.2 g MS salts, 50 g sucrose, 110 µg BAP and 0.02% Silwet L-77 per liter). After 5 minutes, the *Agrobacterium* solution is removed while keeping the polypropylene container in place and the pots returned to an upright position. Pots are then placed in flats (10 pots per flat) containing approximately 1 inch of water and covered with shade cloth. After 24 hours, the shade cloth and polypropylene containers are removed.

After flowering, each pot is covered with a ciber plant sleeve. When plants are completely dry, seed is collected and stored.

3. High Throughput Screening—T1 Generation

Transformed seed are placed in pots containing a water saturated soil miture of Sunshine Mix, Vermiculite, Marathon and Osmocote. Pots are then placed in flats and stored in the dark at 4° C. for at least 2 days. After transferring the flats from the cooler to the greenhouse, they are covered with 55% shade cloth and propagation domes. When the cotyledons are fully expanded the cloth and domes are removed.

Plants are sprayed with a solution of 3 ml concentrated Finale in 48 oz water. Spraying is repeated every 3-4 days until only transformants remain. Transformants are thinned to a maximum of 5 plants per pot.

4. GFP Assay

Tissues are dissected by eye or under magnification using INOX 5 grade forceps and placed on a slide with water and coverslip. An attempt is made to record images of observed expression patterns at earliest and latest stages of development of tissues listed below. Specific tissues will be preceded with High (H), Medium (M), Low (L) designations.

| | |
|---|---|
| Flower | Pedicel, receptacle, nectary, sepal, petal, filament, anther, pollen, carpel, style, papillae, vascular, epidermis, stomata, trichome |
| Silique | Stigma, style, carpel, septum, placentae, transmitting tissue, vascular, epidermis, stomata, abscission zone, ovule |

-continued

| | |
|---|---|
| Ovule | Pre-fertilization: inner integument, outer integument, embryo sac, funiculus, chalaza, micropyle, gametophyte<br>Post-fertilization: zygote, inner integument, outer integument, seed coat, primordial, chalaza, miccropyle, early endosperm, mature endosperm, embryo |
| Embryo | Suspensor, preglobular, globular, heart, torpedo, late, mature, provascular, hypophysis, radicle, cotyledons, hypocotyls |
| Stem | Epidermis, cortex, vascular, xylem, phloem, pith, stomata, trichome |
| Leaf | Petiole, mesophyll, vascular, epidermis, trichome, primordial, stomata, stipule, margin |

T1 Mature: These are the T1 plants resulting from independent transformation events. These are screened between stage 6.50-6.90 (means the plant is flowering and that 50-90% of the flowers that the plant will make have developed) which is 4-6 weeks of age. At this stage the mature plant possesses flowers, siliques at all stages of development, and fully expanded leaves. We do not generally differentiate between 6.50 and 6.90 in the report but rather just indicate 6.50. The plants are initially imaged under UV with a Leica Confocal microscope. This allows examination of the plants on a global level. If expression is present, they are imaged using scanning laser confocal microscopy.

T2 Seedling: Progeny are collected from the T1 plants giving the same expression pattern and the progeny (T2) are sterilized and plated on agar-solidified medium containing M&S salts. In the event that there is no expression in the T1 plants, T2 seeds are planted from all lines. The seedlings are grown in Percival incubators under continuous light at 22° C. for 10-12 days. Cotyledons, roots, hypocotyls, petioles, leaves, and the shoot meristem region of individual seedlings are screened until two seedlings are observed to have the same pattern. Generally found the same expression pattern is found in the first two seedlings. However, up to 6 seedlings are screened before "no expression pattern" is recorded. All constructs are screened as T2 seedlings even if they did not have an expression pattern in the T1 generation.

T2 Mature: The T2 mature plants are screened in a similar manner to the T1 plants. The T2 seeds are planted in the greenhouse, exposed to selection and at least one plant screened to confirm the T1 expression pattern. In instances where there are any subtle changes in expression, multiple plants are examined and the changes noted in the tables.

T3 Seedling: This is done similar to the T2 seedlings except that only the plants for which we are trying to confirm the pattern are planted.

Confirmation of promoter sequence: Promoter construct sequence is 5' verified in T1 mature plants and confirmed in the following generation by 5' and 3' sequencing of the entire promoter of two or 3 events. Sequences from all events are used to generate a consensus sequence. In every case, the sequences of the 2-3 events are matched.

Image Data:

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in PowerPoint specifying organ and specific expressing tissues.

Instrumentation:

An Inverted Leica DM IRB microscope is used with two Fluorescence filter blocks: (1) Blue excitation BP 450-490; long pass emission LP 515 and (2) Green excitation BP 515-560; long pass emission LP 590. The following objectives are used: HC PL FLUOTAR 5x/0.5, HCPL APO 10x/0.4 IMM water/glycerol/oil, HCPL APO 20x/0.7 IMM water/glycerol/oil and HCXL APO 63x/1.2 IMM water/glycerol/oil. A Leica TCS SP2 confocal scanner with a Spectral range of detector optics of 400-850 nm was used with a variable computer controlled pinhole diameter, an Optical zoom 1-32x and four simultaneous detectors: three channels for collection of fluorescence or reflected light and one channel for transmitted light detector. The laser sources are: (1) Blue Ar 458/5 mW, 476 nm/5 mW, 488 nm/20 mW, 514 nm/20 mW, (2) Green HeNe 543 nm/1.2 mW and (3) Red HeNe 633 nm/10 mW.

TABLE 1

Table 1 includes various information about each drought responsive promoter of the invention including the spatial expression promoted by each promoter and the corresponding results from different expression experiments. The sequence for each promoter is set forth in the Sequence Listing.

Table 1 consists of the Promoter Reports for each drought responsive promoter of the invention and provides details for expression driven by each of the nucleic acid drought responsive promoter sequences as observed in transgenic plants. The results are presented as summaries of the spatial expression, which provide information as to gross and/or specific expression in various plant organs and tissues. The observed expression pattern is also presented, which gives details of expression during different generations or different developmental stages within a generation. Additional information is provided regarding the associated gene, the GenBank reference, the source organism of the promoter, and the vector and marker genes used for the construct used to produce the transgenic plant. The following symbols are used consistently throughout the Table:

T1: First generation transformant

T2: Second generation transformant

T3: Third generation transformant (L): low expression level (M): medium expression level (H): high expression level

TABLE 1

Promoter Expression Report #134

Promoter Tested In: *Arabidopsis thaliana*, Wassilewskija (WS) ecotype
Spatial expression summary:
Flower         H anther

TABLE 1-continued

Ovule          L early endosperm L embryo
Embryo        L suspensor L preglobular
Observed expression pattern:
T1 mature: Tapetum cells within developing anther. Not in developing pollen. In addition to taptetum, weak expression in suspensor cells of zygote, free-nuclear and early cellularized endosperm. Not expressed in mature endosperm. Early endosperm expression may not be detected in multiple lines due to weak expression.
T2 Seedling: No expression observed.
Expected expression pattern: Inducible promoter - induced by different forms of stress (e.g. drought and heat).
Gene:                    Strictosidine synthase-related
GenBank: NM_129693 *Arabidopsis thaliana* strictosidine synthase-related (At2g41290) mRNA, complete cds gi|18405658|ref|NM_129693.1|[18405658].
Source Promoter Organism:    *Arabidopsis thaliana*, Columbia (Col) ecotype
Vector:                   pNewbin4-HAP1-GFP
Marker Type:             GFP-ER
Generation Screened:      XT1 Mature X T2 Seedling    ☐T2 Mature    ☐T3 Seedling

| Treatment: | Age: | Gen: | Time points: | Events Screened/ Response | Response: |
|---|---|---|---|---|---|
| 1. Heat 42 C. | 4 wks | T2 | 2 Hr | 2/1 | Yes |
| | | | 6 Hr | 2/1 | Yes |
| | | | 4 Hr post 2 Hr 42 C. | 2/1 | Yes |
| 2. Drought | 4 wks | T2 | 8 days no water | 2/0 | No |

T1 Mature Plant Expression      Organs/Tissues screened
Events Screened:   n = 2       Events Expressing:   n = 2
GFP Expression Detected
X Flower            ☐pedicel ☐receptacle ☐nectary ☐sepal ☐petal ☐filament H anther
                      ☐pollen ☐carpel ☐style ☐papillae ☐vascular ☐epidermis ☐stomata
                      ☐trichome
                      ☐silique
☐Silique            ☐stigma ☐style ☐carpel ☐septum ☐placentae ☐transmitting tissue
                      ☐vascular ☐epidermis ☐stomata ☐abscission ☐zone ☐ovule
X Ovule             Pre-fertilization: ☐primordia ☐inner integument ☐outer integument
                      ☐embryo sac ☐funiculus ☐chalaza ☐micropyle ☐gametophyte
                      Post-fertilization: ☐zygote ☐suspensor ☐embryo sack ☐inner
                      integument ☐outer integument ☐endothelium ☐seed coat ☐primordia
                      ☐chalaza ☐micropyle L early endosperm ☐mature endosperm L
                      embryo
X Embryo           L suspensor L preglobular ☐globular ☐heart ☐torpedo ☐late ☐mature
                      ☐provascular ☐hypophysis ☐radicle ☐cotyledons ☐hypocotyl
☐Stem               ☐epidermis ☐cortex ☐vascular ☐xylem ☐phloem ☐pith ☐stomata
                      ☐trichome
☐Leaf                ☐petiole ☐mesophyll ☐vascular ☐epidermis ☐trichome ☐primordia
                      ☐stomata ☐stipule ☐margin
☐Shoot apical meristem       ☐shoot apical meristem ☐flower primordium
Chalaza (Ch), Endosperm (En), Free nuclear endosperm (FNE), Funiculus (Fn), Micropyle, (Mp), Pollen (Po), Tapetum (Tp), Zygote (Zg), T2 Seedling Expression        Tissues Screened
Events Screened: n = 2        Events Expressing: n = 0
Seedlings expressing/Seedlings screened
Event-02: 0/6
Event-04: 0/6
No GFP Expression Detected Induction Screens
1. Heat
An increased level of GFP expression was observed in flowers and siliques of plants after 2 and 4 hours heat treatment and 24 hours post 2 hour heat treatment relative to control plants. No GFP expression was observed in control lines.
2. Drought
No response observed.
Receptacle (Rc), Silique (Si), Pedicle (Pd)

Construct:                  PT0505 (SEQ ID NO: 1)
Promoter candidate I.D:   11768710
cDNA I.D:                 23544866 (OCKHAM3-CD)
Lines expressing:         PT0505- 02, -04

TABLE 1-continued

Promoter Expression Report #159

Promoter Tested In: *Arabidopsis thaliana*, Wassilewskija (WS) ecotype
Spatial expression summary:
Flower        H stomata H pollen
Silique        H stomata
Stem         H stomata
Leaf          H stomata
Primary Root   L epidermis
Observed expression pattern:
T1 mature: High GFP expression in guard cells throughout mature aerial organs. High GFP expression in pollen.
T2 seedling: Low GFP expression in root epidermal cells near transition zone.
Expected expression pattern:     ABA - Induction >5 fold induction by ABA application
Gene:                             Hypothetical protein
GenBank: NM_104709 *Arabidopsis thaliana* hypothetical protein (At1g60190) mRNA, complete cds gi|18406652|ref|NM_104709.1|[28309481]
Source Promoter Organism:     *Arabidopsis thaliana*, Columbia (Col) ecotype
Vector:                          pNewbin4-HAP1-GFP
Marker Type:              GFP-ER
Generation Screened:     XT1 Mature XT2 Seedling    ☐T2 Mature    ☐T3 Seedling

| Treatment: | Age: | Gen: | Time points: | Events Screened/Response | Response: |
|---|---|---|---|---|---|
| 1. ABA | 14 | T2 | 3 Hr | 2/0 | No |
| 100 uM | days |  | 6 Hr | 2/1 | Yes |
| 2. Drought | 4 wks | T2 | 8 days no water | 2/0 | No |

T1 Mature Plant Expression     Organs/Tissues screened
Events Screened:   n = 2     Events Expressing:   n = 2
GFP Expression Detected
X Flower           ☐pedicel ☐receptacle ☐nectary ☐sepal ☐petal ☐filament ☐anther H
                   pollen ☐carpel ☐style ☐papillae ☐vascular ☐epidermis H stomata
                   ☐trichome
                   ☐silique
X Silique          ☐stigma ☐style ☐carpel ☐septum ☐placentae ☐funiculus ☐transmitting
                   tissue ☐vascular ☐epidermis H stomata ☐abscission zone ☐ovule
☐Ovule            Pre-fertilization: ☐primordia ☐inner integument ☐outer integument
                   ☐embryo sac ☐funiculus ☐chalaza ☐micropyle ☐gametophyte
                   Post-fertilization: ☐zygote ☐suspensor ☐embryo sack ☐funiculus
                   ☐inner integument ☐outer integument ☐endothelium ☐seed coat
                   ☐primordia ☐chalaza ☐micropyle ☐early endosperm ☐mature
                   endosperm ☐embryo
☐Embryo          ☐suspensor ☐preglobular ☐globular ☐heart ☐torpedo ☐late ☐mature
                   ☐provascular ☐hypophysis ☐radicle ☐cotyledons ☐root meristem
                   ☐shoot meristem
X Stem             ☐epidermis ☐cortex ☐interfascicular region ☐vascular ☐xylem ☐phloem
                   ☐pith H stomata ☐trichome
X Leaf              ☐petiole ☐mesophyll ☐vascular ☐epidermis ☐trichome ☐primordia H
                   stomata ☐stipule ☐margin
☐Shoot            ☐shoot apical meristem ☐flower primordium
apical
meristem
Carpel (Ca), Guard cell (Gc), Ovule (Ov), Pollen (Po)

T2 Seedling Expression        Tissues Screened
Events Screened: n = 2      Events Expressing: n = 2
Seedlings expressing/Seedlings screened
Event-01: 3/6
Event-02: 4/6
GFP Expression Detected
☐Hypocotyl         ☐epidermis ☐cortex ☐vascular ☐xylem ☐phloem ☐stomata
☐Cotyledon         ☐mesophyll ☐vascular ☐epidermis ☐margin ☐petiole ☐stomata
                   ☐hydathode
☐Rosette Leaf     ☐mesophyll ☐vascular ☐epidermis ☐trichome ☐petiole
                   ☐primordia ☐stomata ☐stipule ☐margin ☐hydathode
X Primary Root   L epidermis ☐trichoblast ☐atrichoblast ☐cortex ☐endodermis
                   ☐vascular ☐xylem ☐phloem ☐pericycle ☐quiescent
                   ☐columella ☐root cap ☐root hairs
☐Lateral root      ☐epidermis ☐trichoblast ☐atrichoblast ☐cortex ☐endodermis
                   ☐initials ☐flanking cells ☐vascular ☐lateral root cap

TABLE 1-continued

☐Shoot apical meristem   ☐shoot apical meristem
Epidermis (Ep), Hypocotyle (Hy), Root (Rt)

Induction Screens
1. ABA 100 uM
An increased level of GFP expression was observed in leaf, hypocotyls of seedlings treated with ABA relative to control seedlings.
2. Drought
No response was observed.

Construct:            PT0561 (SEQ ID NO: 2)
Promoter candidate I.D:   11768758
cDNA I.D:             23519995
Lines expressing:     PT0561 -01, 02

Promoter Expression Report #183

Promoter Tested In: *Arabidopsis thaliana*, Wassilewskija (WS) ecotype
Spatial expression summary:
Flower        M pedicel M receptacle M sepal M vascular H stomata
Silique       H funiculus
Ovule         Pre-fertilization: H inner integument H endothelium
Stem          H vascular
Leaf          H stomata
Cotyledon     L vascular L epidermis M hydathode
Primary Root  H epidermis H cortex L vascular
Observed expression pattern:
T1 mature: GFP expressed in vasculature of young floral buds of the inflorescence and stem. GFP expressed in inner integument cell layer of ovules and endothelium of mature seeds. GFP highly expressed in the distal funiculus at the ovule junction site. Guard cell expression throughout all organs.
T2 seedling: High GFP expression throughout root epidermis and cortex cells with lower expression in vasculature. Low GFP expression in vasculature and epidermal cells related to hydathode glands in cotyledons.
Expected expression pattern:   Drought inducible - Up regulated In Drought Condition
Gene:                          Protein phosphatase 2C, putative/PP2C, putative
GenBank: NM_111974 *Arabidopsis thaliana* protein phosphatase 2C, putative/PP2C, putative (At3g11410) mRNA, complete cds gi|30681716|ref|NM_111974.3|[30681716]
Source Promoter Organism:      *Arabidopsis thaliana*, Columbia (Col) ecotype
Vector:                        pNewbin4-HAP1-GFP
Marker Type:                   GFP-ER
Generation Screened:   XT1 Mature XT2 Seedling   ☐T2 Mature   ☐T3 Seedling

| Treatment: | Age: | Gen: | Time points: | Events Screened/Response | Response: |
|---|---|---|---|---|---|
| 1. Drought | 4 wks | T2 | 8 days no water | 2/2 | Yes |

T1 Mature Plant Expression     Organs/Tissues screened
Events Screened:  n = 3        Events Expressing:  n = 2
GFP Expression Detected
X Flower      M pedicel M receptacle ☐nectary M sepal ☐petal ☐filament ☐anther
              ☐pollen ☐carpel ☐style ☐papillae M vascular ☐epidermis H stomata
              ☐trichome
              ☐silique
X Silique     ☐stigma ☐style ☐carpel ☐septum ☐placentae H funiculus
              ☐transmitting tissue ☐vascular ☐epidermis ☐stomata ☐abscission zone
              H ovule
X Ovule       Pre-fertilization: ☐primordia ☐inner integument ☐outer integument
              ☐embryo sac ☐funiculus ☐chalaza ☐micropyle ☐gametophyte
              Post-fertilization: ☐zygote ☐suspensor ☐embryo sack H inner
              integument ☐outer integument H endothelium ☐seed coat ☐primordia
              ☐chalaza ☐micropyle ☐early endosperm ☐mature endosperm ☐embryo
☐Embryo       ☐suspensor ☐preglobular ☐globular ☐heart ☐torpedo ☐late ☐mature
              ☐provascular ☐hypophysis ☐radicle ☐cotyledons ☐hypocotyl
X Stem        ☐epidermis ☐cortex H vascular ☐xylem ☐phloem ☐pith ☐stomata
              ☐trichome
X Leaf        ☐petiole ☐mesophyll ☐vascular ☐epidermis ☐trichome ☐primordia H
              stomata ☐stipule ☐margin
☐Shoot        ☐Shoot apical meristem ☐Flower primordium
apical
meristem
Carpel (Ca), Endothelium (Ed), Funiculus (Fn), Guard cell (Gc), Inner integument (Ii), Ovule (Ov), Vascular bundle (Vb), Vascular (Vs)

TABLE 1-continued

T2 Seedling Expression  Tissues Screened
Events Screened: n = 2  Events Expressing: n = 2
Seedlings expressing/Seedlings screened
Event-01: 5(6)
Event-03: 2(5)
GFP Expression Detected
☐Hypocotyl         ☐epidermis ☐cortex ☐vascular ☐xylem ☐phloem ☐stomata
X Cotyledon        ☐mesophyll L vascular L epidermis ☐margin ☐stomata
                   M hydathode
☐Rosette Leaf      ☐mesophyll ☐vascular ☐epidermis ☐trichome ☐petiole
                   ☐primordia ☐stomata ☐stipule ☐margin ☐hydathode
X Primary Root     H epidermis ☐trichoblast ☐atrichoblast H cortex ☐endodermis
                   L vascular ☐xylem ☐phloem ☐pericycle ☐quiescent
                   ☐columella ☐root cap ☐root hairs
☐Lateral root      ☐epidermis ☐trichoblast ☐atrichoblast ☐cortex ☐endodermis
                   ☐initials ☐flanking cells ☐vascular ☐lateral root cap
☐Shoot apical      ☐Shoot apical meristem
meristem
Cortex (Cr), Epidermis (Ep), Guard cell (Gc), Hydathode (Hd), Vascular (Vs)
Induction Screens 1. Drought    T2 mature
An increase in GFP expression under drought conditions was observed in two events
of promoter line PT0688. An increased in GFP expression in response drought was seen in the
stem, leaf and flower relative to the corresponding organs from control plants.

Construct:              PT0688 (SEQ ID NO: 3)
Promoter candidate I.D: 15371509
cDNA I.D:               23431527
Lines expressing:       PT0688 -01, -03

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

Each of the following co-pending applications, cited above, is hereby expressly incorporated by reference in its entirety: U.S. application Ser. No. 11/298,391, filed on Dec. 8, 2005 entitled "Nucleotide Sequences and Corresponding Polypeptides Conferring Modulated Plant Size and Biomass in Plants"; U.S. application Ser. No. 11/305,666 filed on Dec. 15, 2005 entitled "Nucleotide Sequences and Corresponding Polypeptides Encoded Thereby Useful for Enhancing Plant Drought Tolerance" and U.S. application Ser. No. 11/228,587 filed Sep. 16, 2005.

What is claimed is:

1. An isolated drought responsive promoter that drives transcription in plants, consisting of a nucleic acid molecule of SEQ ID NO. 3.

2. A vector comprising a) a first nucleic acid molecule consisting of a nucleic acid molecule of SEQ ID NO. 3; and b) a second nucleic acid molecule, whereby said first and second nucleic acid molecules are operably linked.

3. The vector of claim 2 wherein said first and second nucleic acid molecules are heterologous to each other.

4. A plant cell transformed with a first nucleic acid molecule that consists of a nucleic acid molecule of SEQ ID NO. 3.

5. The plant cell according to claim 4, further comprising a second nucleic acid molecule, whereby first and second nucleic acid molecules are operably linked.

6. A transgenic plant obtained from the plant cell of claim 4 or claim 5.

7. A tissue obtained from the transgenic plant of claim 6, wherein said tissue comprises the first nucleic acid molecule.

8. The transgenic plant according to claim 6, wherein said first nucleic acid sequence is operably linked to said second nucleic sequence and whereby said transgenic plant has increased drought tolerance compared to an untransformed and naturally occurring plant of the same species cultivated under the same conditions.

9. The transgenic plant according to claim 8, whereby said transgenic plant has increased biomass or higher seed yield compared to an untransformed and naturally occurring plant of the same species cultivated under the same conditions.

10. The transgenic plant according to claim 8, whereby said transgenic plant is tolerant to cold, drought, or salt compared to an untransformed and naturally occurring plant of the same species cultivated under the same conditions.

11. The transgenic plant according to claim 8, whereby said transgenic plant has enhanced water uptake compared to an untransformed and naturally occurring plant of the same species cultivated under the same conditions.

12. The progeny of the transgenic plant of claim 6, wherein said progeny comprises the first nucleic acid molecule.

* * * * *